(12) United States Patent
Stangler et al.

(10) Patent No.: US 11,730,683 B2
(45) Date of Patent: *Aug. 22, 2023

(54) FLAVORED WIPE AND DISPENSING SYSTEM

(71) Applicant: TaylorBaby, LLC, Castle Rock, CO (US)

(72) Inventors: Danielle R. Stangler, Castle Rock, CO (US); Julia M. Rossi, Aurora, CO (US); Ryan Stangler, Castle Rock, CO (US)

( * ) Notice: Subject to any disclaimer, the term of this patent is extended or adjusted under 35 U.S.C. 154(b) by 1020 days.

This patent is subject to a terminal disclaimer.

(21) Appl. No.: 14/635,130

(22) Filed: Mar. 2, 2015

(65) Prior Publication Data
US 2015/0174015 A1 Jun. 25, 2015

Related U.S. Application Data

(63) Continuation-in-part of application No. 13/659,455, filed on Oct. 24, 2012, now Pat. No. 9,822,489.

(60) Provisional application No. 61/552,569, filed on Oct. 28, 2011.

(51) Int. Cl.
| | | |
|---|---|---|
| A61K 8/97 | (2017.01) | |
| A61K 8/02 | (2006.01) | |
| A61Q 19/10 | (2006.01) | |
| A61Q 19/00 | (2006.01) | |
| A61Q 19/08 | (2006.01) | |
| C11D 17/04 | (2006.01) | |
| C11D 3/382 | (2006.01) | |
| D21H 21/14 | (2006.01) | |
| D21H 27/00 | (2006.01) | |
| A61K 8/60 | (2006.01) | |
| B65D 85/07 | (2017.01) | |
| A61K 8/9789 | (2017.01) | |

(52) U.S. Cl.
CPC ............ *A61K 8/0208* (2013.01); *A61K 8/602* (2013.01); *A61K 8/9789* (2017.08); *A61Q 19/00* (2013.01); *A61Q 19/08* (2013.01); *A61Q 19/10* (2013.01); *B65D 85/07* (2018.01); *C11D 3/382* (2013.01); *C11D 17/049* (2013.01); *D21H 21/14* (2013.01); *D21H 27/002* (2013.01)

(58) Field of Classification Search
None
See application file for complete search history.

(56) References Cited

U.S. PATENT DOCUMENTS

| | | |
|---|---|---|
| 5,110,801 A | 5/1992 | Leveen et al. |
| 5,320,772 A | 6/1994 | Tricca |
| 6,361,784 B1 | 3/2002 | Brennan et al. |
| 6,378,698 B1 | 4/2002 | Scoggins |
| 6,486,104 B2 | 11/2002 | Patzer et al. |
| 6,821,940 B2 | 11/2004 | Bullock et al. |
| 7,201,271 B1 | 4/2007 | Saad |
| 7,497,351 B2 | 3/2009 | Amundson et al. |
| 7,674,058 B2 | 3/2010 | Sharp et al. |
| 7,735,682 B1 | 6/2010 | Cassel et al. |
| 7,943,165 B2 | 5/2011 | Doney et al. |
| 8,632,636 B1 | 1/2014 | Tricca et al. |
| 2002/0127937 A1 | 9/2002 | Lange et al. |
| 2002/0164910 A1 | 11/2002 | Murray |
| 2004/0031120 A1 | 2/2004 | Cherian |
| 2004/0071754 A1 | 4/2004 | Jupiter |
| 2005/0074483 A1 | 4/2005 | Lange |
| 2005/0079327 A1 | 4/2005 | Stiles |
| 2006/0078515 A1 | 4/2006 | Kamrin-Balfour |
| 2006/0151518 A1 | 7/2006 | Sarbo et al. |
| 2006/0193898 A1 | 8/2006 | Norman |
| 2007/0278242 A1 | 12/2007 | Amundson et al. |
| 2007/0289988 A1 | 12/2007 | Sosalla et al. |
| 2008/0038413 A1 | 2/2008 | Northrop |
| 2008/0064278 A1 | 3/2008 | Oaroche |
| 2008/0112902 A1 | 5/2008 | Perechocky |
| 2008/0226803 A1 | 9/2008 | Letourneau et al. |
| 2008/0311166 A1 | 12/2008 | Wimer |
| 2009/0004355 A1 | 1/2009 | Catani |
| 2009/0286437 A1 | 11/2009 | Cunningham et al. |
| 2012/0090113 A1 | 4/2012 | Manifold et al. |
| 2013/0071887 A1 | 3/2013 | Wehrli |
| 2013/0108722 A1 | 5/2013 | Stangler et al. |
| 2014/0127152 A1 | 5/2014 | Goralczyk et al. |
| 2014/0227421 A1 | 8/2014 | Markosyan |
| 2015/0011493 A1 | 1/2015 | Laboureau et al. |

(Continued)

FOREIGN PATENT DOCUMENTS

| | | |
|---|---|---|
| CN | 103040688 | 4/2013 |
| JP | 08325156 | 12/1996 |
| JP | H08325156 | 12/1996 |

(Continued)

OTHER PUBLICATIONS

Chart of Sweeteners, 2014, 1 page.
"High Potency Sweeteners," Sweet Green Fields, 2014, 1 page.
"Teeth Wipes by Confident White Smile: A Healthy Alternative for a Healthy Lifestyle," DMS Smile, Windsor, Ontario, Canada, 2014, retrieved from www.tcwipes.com, 2 pages.

(Continued)

*Primary Examiner* — Terry A McKelvey
*Assistant Examiner* — Catheryne Chen

(57) ABSTRACT

A flavored wipe and method of manufacturing and dispensing the flavored wipe includes a solution of water and a flavoring component, especially those including a sweetener, such as stevia or other natural or artificial sweeteners. Flavored wipes may be dispensed from a system that includes a compartment to hold material configured for use as a wipe and that includes a solution with at least a flavoring component, with such dispenser having an opening in a compartment to dispense such wipes.

20 Claims, 7 Drawing Sheets

(56) References Cited

U.S. PATENT DOCUMENTS

2015/0050410 A1 2/2015 Luo et al.
2015/0174015 A1 6/2015 Stangler et al.

FOREIGN PATENT DOCUMENTS

| JP | 2008-037758 | 2/2008 |
|---|---|---|
| JP | 2011-126795 | 6/2011 |
| WO | WO 1998/17239 | 4/1998 |
| WO | WO 02/060419 | 8/2002 |
| WO | WO 2005/089782 | 9/2005 |
| WO | WO 2007/027269 | 3/2007 |
| WO | WO 2007/094312 | 8/2007 |
| WO | WO 2008/134828 | 11/2008 |
| WO | WO 2009/071277 | 6/2009 |
| WO | WO 2010/017081 | 2/2010 |
| WO | WO 2013/063102 | 5/2013 |

OTHER PUBLICATIONS

Das et al., "Evaluation of safety and efficacy of Stevia Moisturiser Gel by Clinical Trial," Global J Medicinal Plant Res., 2013, vol. 1(2), pp. 228-233.
International Search Report for International Patent Application No. PCT/US2012/061673, dated Mar. 18, 2013, 3 pages.
Written Opinion for International Patent Application No. PCT/US2012/061673, dated Mar. 18, 2013, 9 pages.
Official Action for U.S. Appl. No. 13/659,455, dated Aug. 1, 2014, 11 pages.
Response to Official Action (dated Mar. 23, 2016) for Canadian Patent Application No. 2.888,009, dated Sep. 16, 2016, 10 pages.
Notice of Allowance for Canadian Patent Application No. 2,888,009, dated Nov. 9, 2016, 1 page.
Official Action for Canadian Patent Application No. 2,888,009, dated Mar. 23, 2016, 4 pages.
Official Action for U.S. Appl. No. 13/659,455, dated Nov. 29, 2013, 7 pages, Restriction Requirement.
Final Action for U.S. Appl. No. 13/659,455, dated Sep. 24, 2015, 12 pages.

FLAVORED WIPE AND DISPENSING SYSTEM

PRIORITY CLAIM

This application is a continuation-in-part application to U.S. patent application Ser. No. 13/659,455, filed on Oct. 24, 2012, which claims priority to, and the benefit of, U.S. Provisional Patent Application No. 61/552,569 filed Oct. 28, 2011 and titled "Wet Wipe" of Danielle R. Stangler and Ryan Stangler, both of which are hereby incorporated by reference in their entirety as though fully set forth herein.

BACKGROUND

Babies and toddlers inevitably get dirty faces. As a result, it is necessary to clean their faces frequently from time to time. However, babies and toddlers can also be fussy when it is time for their faces to be cleaned. Babies can practice several modes of "face wiping avoidance" and as a result, it can be a frustrating experience for a parent who is trying to clean his/her baby's face only to have the child turn away, scream, squirm, wiggle away, and generally resist having his/her face cleaned.

Moreover, children have very sensitive skin. This is particularly true of the facial area of the child. So, the frequent process of cleaning a child's facial area can result in irritation to the skin. This only adds to the further avoidance of the face wiping process by the child. If the skin gets irritated, it may become physically uncomfortable for the child to have their face wiped.

SUMMARY

There is currently the unsolved problem of how to clean a user's face effectively when the user (particularly a child) is being fussy. And there is also the problem of how to reduce or altogether eliminate irritating the user's skin. In accordance with an embodiment, a wet wipe is provided with flavoring. The flavoring can include a natural component, such as the natural flavoring known as stevia. (For purposes of this application, the word stevia is intended to have a broad meaning so as to encompass all types of stevia extracts, derivatives, solutions, or solids that are acceptable as additives for sweeteners or moisturizers unless specified with more particularity herein.) The stevia flavored wet wipe can provide a limited sweet taste for the wet wipe that does not create a negative impression on the child. Thus, when the parent goes to wipe the face of the child, the child does not resist being wiped with the wet wipe around the mouth area because the child knows that any trace solution imparted by the wet wipe will not taste bad—whether from direct contact with the wet wipe or from the residue left behind from the wet wipe solution on the child's face. Moreover, the wet wipe flavored with stevia will not leave behind a substantially sticky residue. Unlike sugar based products that do leave behind a sticky residue, stevia does not produce a sticky residue and therefore can serve as a useful cleaning additive as described herein.

In accordance with another embodiment, a wet wipe is provided with a moisturizer and/or soothing agent, such as the natural component known as stevia. The moisturizing and/or soothing properties of stevia allow the wet wipe to moisturize and/or soothe the skin of the child at the same time that the child is being cleaned with the wet wipe. So, not only is the child's face cleaned but it is moisturized and/or soothed at the same time. This has the opposite effect from most other wet wipes, because other wet wipes can actually irritate and/or damage a child's skin when the child's face is cleaned due to the materials of those wet wipes and solutions of the wet wipes. Yet another embodiment provides a wet wipe carrying a stevia solution that is formulated so as not to taste bad but also moisturizes the child's face. Further embodiments will also be apparent from the following disclosure.

DETAILED DESCRIPTION

As noted above, children can be very prone to getting their faces dirty while at the same time fussy when they need to have their faces cleaned. The child can get dirty from being fed, eating on their own, or playing in general. As a result, from time to time the child's face needs to be cleaned by a parent or caregiver. Some children resist being cleaned because they are generally fussy. Others have learned from experiences with other types of wet wipes that a bad taste or unpleasant sensation is encountered with those other types of wet wipes. For example, some wipes leave behind a bad tasting residue on the child's mouth area that tastes bad to the child. As a result, children are currently very resistant to having their faces cleaned in general and particularly cleaned by existing types of wet wipes.

In accordance with one embodiment of the invention, this notorious problem has finally been solved by providing the wet wipe with a natural flavoring known as stevia and sometimes referred to as stevia extract, as will be described in more detail below with reference to various example implementations. Briefly, however, a wet wipe may be configured to carry a stevia extract solution. The wipe may be used as an applicator to apply stevia extract to human skin. The pleasant taste of the stevia solution diminishes the fussiness by a user (e.g., a child or even an adult) when the user's face is wiped with the wipe. The wipe can also be used as a "sit still wipe," for example where the child licks the wipe while getting their diaper changed. The stevia extract solution can also be used to moisturize the user's skin.

In an example, a wet wipe is disclosed, including a material configured for use as a wipe; wherein the material carries a solution comprising water and a stevia extract. In another example, a method of cleaning the face of a child is disclosed, including wiping the face of the child with a wipe carrying a pre-determined solution comprising water and stevia extract. In another example, a method of moisturizing human skin is disclosed, including utilizing a wipe carrying a solution comprising a stevia extract to wipe the solution onto the skin. Still other examples will be apparent to those having ordinary skill in the art after becoming familiar with the teachings of the following disclosure.

Before continuing, it is noted that as used herein, the terms "includes" and "including" mean, but is not limited to, "includes" or "including" and "includes at least" or "including at least." The term "based on" means "based on" and "based at least in part on."

Figure 1:
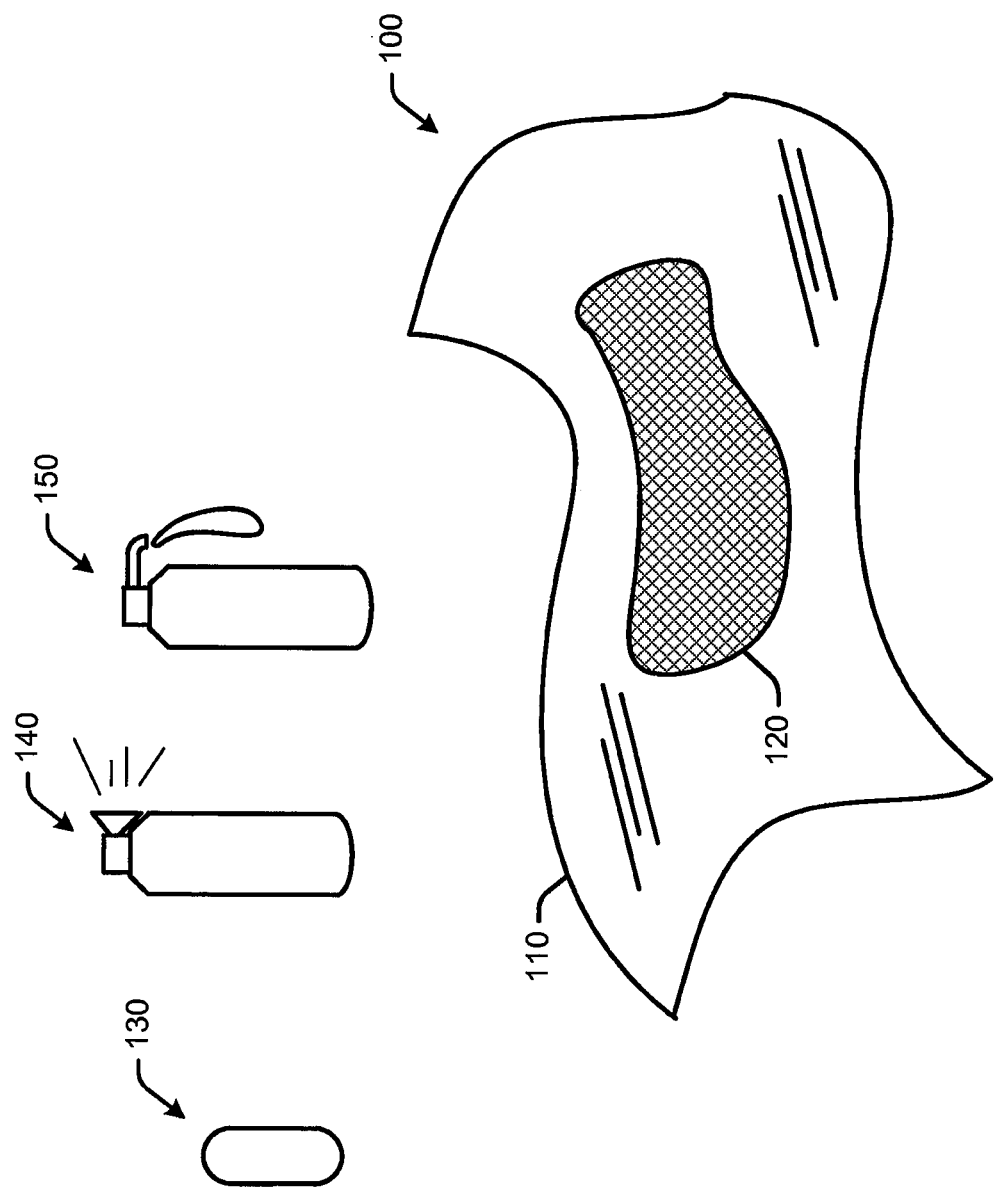
FIG. 1 is a perspective view of an example flavored wipe.

FIG. 1 is a perspective view of an example flavored wipe 100.

Figure 2:
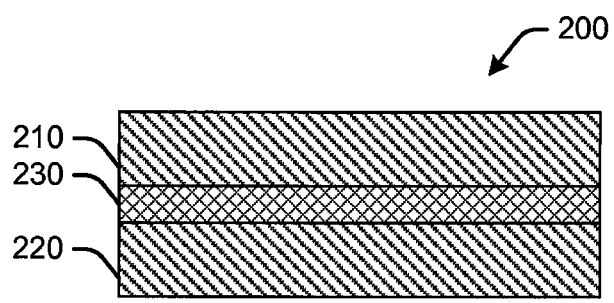
FIG. 2 is a cross-sectional view of an example flavored wipe such as the flavored wipe shown in FIG. 1.

FIG. 2 is a cross-sectional view of an example flavored wipe 200, such as the flavored wipe shown in FIG. 1. The flavored wipe 100 (or 200) may include a material 110 configured for use as a wipe, and a solution (illustrated in FIG. 1 by outline 120) comprising water and a flavoring component.

It is noted that the solution 120 may impregnate the entire wipe and/or only a portion of the wipe. For example, the solution may be provided on a corner of the wipe. Examples of the solution 120 will be described in more detail below. Briefly, however, the flavoring component may be a stevia extract.

The solution 120 may also include a cleaning agent, a moisturizing agent, a coloring agent, and/or a scenting agent. For example, the wipe 100 (or 200) may be a dual purpose (or multi-purpose) wipe, wherein a part of the wipe (e.g., a side or corner) includes a moisturizing agent and another part of the wipe (e.g., opposite side or corner) includes the flavoring component, and so forth. By way of illustration, half a single wipe 100 may be colored blue to indicate use as a hand cleaner (and thus include the cleaning agent) and the other half of the same wipe 100 may be colored green to indicate use as a flavored wipe (and thus include the flavoring component). Such an illustration may be desirable when the cleaner is for cleaning hands but should not be put in the mouth (e.g., the child's mouth, or even an adult's mouth such as for wiping teeth).

In an example, the material 110 is a dry compressed wipe and the solution (or at least the flavoring component) is added to the material from a vial (not shown) or a capsule 130. That is, the solution may be encapsulated and dissolved on the material (or separately dissolved and then applied to the material). In another example, the solution (or at least the flavoring component) is added to the material by spraying, for example with spray canister 140. The solution may also be evaporated from the material during manufacture, and the flavoring component is then activated prior to use by rehydration (e.g., by spraying water or other aqueous solution as illustrated by canister 140). In yet another example, the solution is emulsified and dispensed as a cream or lotion as illustrated by pump dispenser 150. The emulsified solution may also be dispensed from a squeezable tube having a small hole (or multiple holes in the cap), or provided in a "makeup" type compact for dipping the material into.

As illustrated in FIG. 2, the wipe may include a material such as a fiber-based textile 200 with fibers forming an outward raised/embossed texture on a first side 210 and/or second or opposite side 220. The fibers may be provided to remove/exfoliate skin during application of the solution on the skin. In an example, the solution may be provided in a separate layer 230. While three layers 210, 220, and 230 are shown in FIG. 2, it is noted that the material is not limited to any particular number of layers. Nor is the material is not limited to having separate layers. Also incorporated by reference in their entirety are U.S. Patent Publication No. 2002/0127937 to Lange et al., U.S. Patent Publication No. 2006/0151518 to Sarbo et al., U.S. Pat. No. 6,361,784 to Brennan et al. and U.S. Patent Publication No. 2012/0090113 to Manifold.

Also disclosed herein is a method of manufacturing a flavored wipe. In an example, the method may include providing a material (e.g., 110 in FIG. 1) configured for use as a wipe, and providing a solution (e.g., 120 in FIG. 1) for the material. The solution includes at least a flavoring component. As discussed above, the method may include providing the solution in dry form and activating the flavoring component immediately prior to use.

The stevia extract can be put into a solution that provides a sufficient amount of stevia extract per volume of water and with sufficient preservatives so as to resist degradation. For example, degradation can be resisted by making the wipe and/or solution resistant to microbial growth and/or pathogen growth. The amount of stevia extract added per volume of water (or volume of another non-harmful solution) should be sufficient to provide a sweet taste. For example, it should be sufficiently sweet that a majority (or a commercially significant minority) of children of a pre-determined age would rate the taste as "not bad" when surveyed. Alternatively, it could be manufactured with a sufficient sweetness that a majority (or commercially significant minority) of purchasing adults would rate the taste as "not bad." A taste that is rated as "not bad" is not necessarily "good" tasting. Rather, it is a taste that one would not try to avoid. Hence, the solution could be formulated to provide a taste that is not objectionable to a child—but not something that a child would try to ingest.

In accordance with one embodiment, the stevia solution can be prepared by combining stevia extract, such as Rebaudioside-A stevia, so that the stevia extract contributes 0.1 to 0.5% by weight of the final solution and the water accounts for the remaining percentage by weight.

Preservatives, such as potassium sorbate, sodium benzoate, and decyl glycoside can be added in appropriate amounts to prevent degradation of the stevia solution.

Other types of stevia and artificial or natural sweeteners could be used as well. For example, there are at least 240 different types of stevia. Some possible types for use in this product are believed to be Rebaudioside-A, Rebaudioside-C, Rebaudioside-D, and Stevioside.

In an example, the flavoring component may be a natural sweetener, selected from the group including but not limited to: stevia, Luo han guo, Mogrosides, Monk Fruit, Monatin (from Sclerochiton ilicifolius plant), Cyclamate, and Brazzein.

In an example, the flavoring component may be an artificial sweetener, selected from the group including but not limited to: Sorbitol, Cyclamate, Saccharin, Aspartame, Sucralose, Acesulfame K, Acesulfame potassium, Neotame, Advantam, Isomtitol, mannitol, Lactitol, Isomalt, and lactitol.

In another embodiment, a solution can be mixed in the following contributions by weight percentage of the final product (e.g., 92.7% of the weight of the final product could be water). An example is illustrated in Table I.

TABLE I

Example Solution

| Component | Contribution (% by weight) |
|---|---|
| Water | 92.7-97.1 |
| Glycerin | 2.5-5.0 |
| Potassium Sorbate | 0.1-0.5 |
| Laurylglucosides Hydroxypropyl Sulfonate | 0.1-0.5 |
| *Lonicera Caprifolium* (Honeysuckle) Flower Extract (and) *Lonicera Japonica* (Honeysuckle) Flower Extract | 0.1-.05 |
| Stevia | 0.1-0.5 |
| Citric Acid | 0.0-0.3 |

Of course, more or less water could be used for example, if some of these components are omitted or changed in amount.

The wet wipes can be prepared by utilizing nonwoven cloth suitable for absorbing solution. A roll of the cloth, preferably with pre-formed lengths of cloth suitable for use as wipes, can then be impregnated with the solution, for example. This is currently well-known by those of ordinary skill in the art. In accordance with one embodiment, the wipe material can be made from biodegradable material so that the wipe will degrade after being disposed of.

Another problem that is faced by parents who currently use wet wipes for children is that those wet wipes can irritate the child's skin—especially after repeated wiping of a child's face over time. This obviously damages the child's skin and makes it more sensitive to future wiping. Plus, it can reinforce the child's aversion to being wiped if the process is painful or irritating to the child.

In accordance with one embodiment, this problem has finally been solved by utilizing the natural moisturizer stevia to moisturize and/or soothe the child's skin at the same time that the child's skin is being cleaned. Thus, the wet wipe with a stevia extract moisturizer, for example, is able to both clean and moisturize the child's skin at the same time.

In accordance with the embodiment where moisturizing is desired, the amount of stevia extract added to the solution can be selected so as to provide a desired moisturizing capability. This may be the same amount or a different amount needed to achieve a desired taste from the solution. So, for example, where the product is intended for use solely as a moisturizing product, one might choose to add more stevia extract so as to produce a greater moisturizing effect on the skin. A similar approach could be followed to achieve a soothing function on the skin.

In accordance with another embodiment, additional additives can be added. For example, as noted above, preservatives may be added to protect the wipe/solution combination from degrading. One example of a preservative is honeysuckle extract. In addition, additives such as vitamin E, chamomile, aloe vera, polysorbate 80, annatto Extract, or natural oils might be added for the properties that those additives provide. For example, orange oil may be added for providing a scent, as well as an antibacterial function. In addition, sugarnate and/or polysorbate 80 can be used as a surfactant. Also, sodium benzoate can be used as a preservative. Green tea extract and aloe vera juice/extract may also be used.

In some embodiments, one might choose to use glycerin in addition to water. Glycerin can be used for its cleaning effect and non-toxic nature if consumed. Glycerin can also provide a moisturizing effect. However, glycerin is believed to have a disagreeable taste to children. So, it may be necessary to add more stevia than that required for water alone to mask the taste of the glycerin, should glycerin be used. It is noted that preservatives are the bad tasting parts of the formula. Glycerin also has a "soapy" taste. But stevia (or other sweeteners discussed herein) imparts a better taste.

In addition for use on a child's face, the wet wipes with moisturizing capability described herein can also be used on other parts of a child's skin. Moreover, they can be used by adults. Possible uses include, wipes for removing make-up; wipes for moisturizing adult skin; wipes for use during or after exercising; wiping the mouth of musical instruments; adding sweet flavor to the skin or other surfaces, wiping the faces of patients at hospitals, skilled nursing facilities, hospice care facilities, and nursing home facilities. Generally, the wipes may be used as non-durable consumer goods, cosmetic products, personal hygiene products, and baby products, for example.

In accordance with one embodiment, the wipe treated with stevia (or other sweetener) solution may be used as an applicator to human skin. For example, it might be used to apply the stevia extract to the face of an older person. Others have asserted that stevia can: help smooth out wrinkles; help heal skin blemishes and acne; help tighten skin like a facial mask; help hydrate skin (more than three times better than glycerin); can help enhance fragrances; can help provide anti-bacterial effect so as to improve shelf-life; help eliminate dandruff; can help treat seborrhea, dermatitis, and eczema. Thus, a wipe treated with stevia is a highly efficient way to apply stevia to the skin and particularly to the facial area that does not appear to have been appreciated by others.

In accordance with another embodiment, a wet wipe may be provided with antimicrobial and anti-pathogen properties by using stevia as part of the solution that is imparted on the wet wipe. stevia has been asserted to exhibit antimicrobial and anti-pathogen properties. Thus, by using it as part of a solution for a wipe product, it is believed that a longer shelf life can be provided for the wipe product. Moreover, this can be accomplished through the use of a natural agent, such as stevia.

To prepare the wet wipes with the stevia solution, one may submerge a roll of wipe material within the stevia solution and allow it to soak for a sufficient time period to allow the solution to be imparted onto or impregnated within the wipe material. Alternatively, the solution may be sprayed or pumped onto the wipe material.

Thus, the use of stevia in a wipe product can address different problems. It can provide a taste that is not unpleasant, so that children will not avoid being wiped with the wipe. It is noted that sugar or other like sweeteners may leave a sticky residue behind. But the use of stevia (or other sweeteners disclosed herein) can provide the desired taste without leaving behind a sticky residue on a child's face. It can provide a soothing and/or moisturizing effect to human skin that counters the effects of a wipe irritating or damaging human skin. And, it can prolong shelf-life by exhibiting antimicrobial and/or anti-pathogen functions. Any of these functions independently or in various combinations can be useful in providing an improved wet wipe product.

Figure 3:
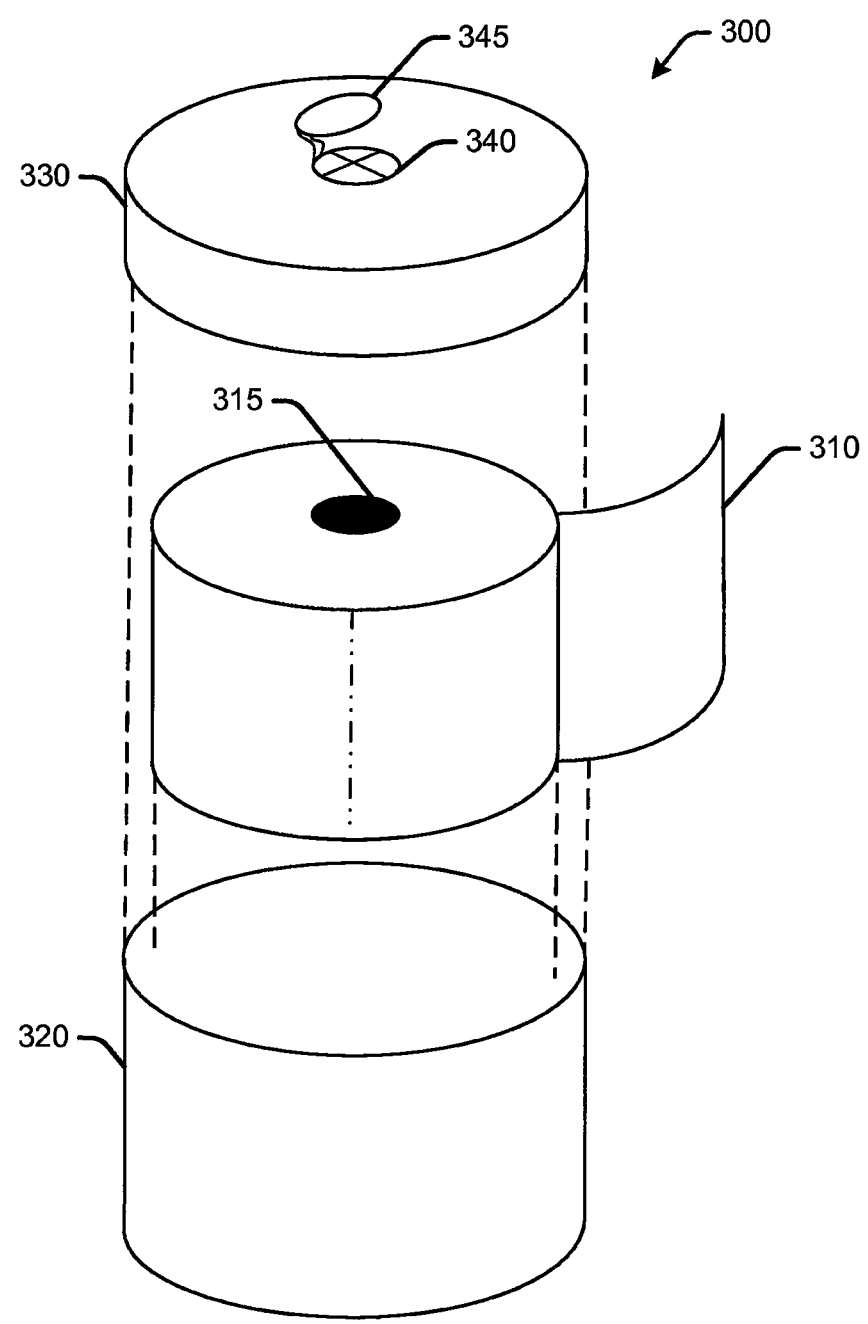
FIG. 3 is an exploded perspective view of an example dispensing system for a flavored wipe.

FIG. 3 is an exploded perspective view of an example dispensing system 300 for a flavored wipe 310. The dispensing system 300 may be any suitable shape and/or size. For example, the dispensing system 300 may be used as a diaper changing table canister. The dispensing system 300 may be fastened in any suitable manner, such as using hook-and-loop (VELCRO™) adhesive, sewn in place, clipped, etc. to a changing table or stroller, diaper bag, messenger bag, car seat, seat in a car, computer, tablet device, cell phone, purse, purse strap, fanny pack, belt loop, table, table in a restaurant, grocery cart, high chair, play gym, etc.

The dispensing system 300 may include a compartment 320 to hold a material configured for use as a wipe 310 including a solution with at least a flavoring component.

The compartment 320 may be a hard container, or a soft-side pouch. In FIG. 3, the wipes 310 are shown as the wipes may be provided on a roll 315. The wipes 310 may be manually removed from the compartment 320 (e.g., by pulling) or automatically dispensed (e.g., using an electronic motor to turn the roll 315). The wipes 310 may be dispensed via a ticket-type dispenser (e.g., pull and tear), and even dispensed as part of a coin-operated system.

The wipes 310 are also shown on the roll 315 as the wipes 310 may be perforated for easy removal as the wipes 310 are pulled through the opening 340. However, the dispensing system 300 is not limited to use with wipes 310 on a roll 315. Other examples include, but are not limited to, precut and folded interlocking sheets, a napkin-type wipe (and "napkin" dispenser), or even a roll of individually packaged sachet pouches attached to each other by perforation.

The compartment may include a lid 330 with an opening 340 formed in the compartment to dispense the wipe 310 from the compartment 320. In an example, the opening may be slotted so as to reduce or altogether prevent evaporation of aqueous solution in the compartment 320. The opening may also be closed, e.g., as illustrated by closure flap 345.

In an example, the solution may be impregnated in the material prior to dispensing the wipes 310 from the compartment 320. In another example, the solution may be dried on the wipes 310 and activated by rehydrating the wipes 310 after dispending from the compartment 320. In yet another example, the solution may be added to dry wipes 310 (e.g., via the mechanisms illustrated in FIG. 1) after dispensing from the compartment 320.

Figure 4:
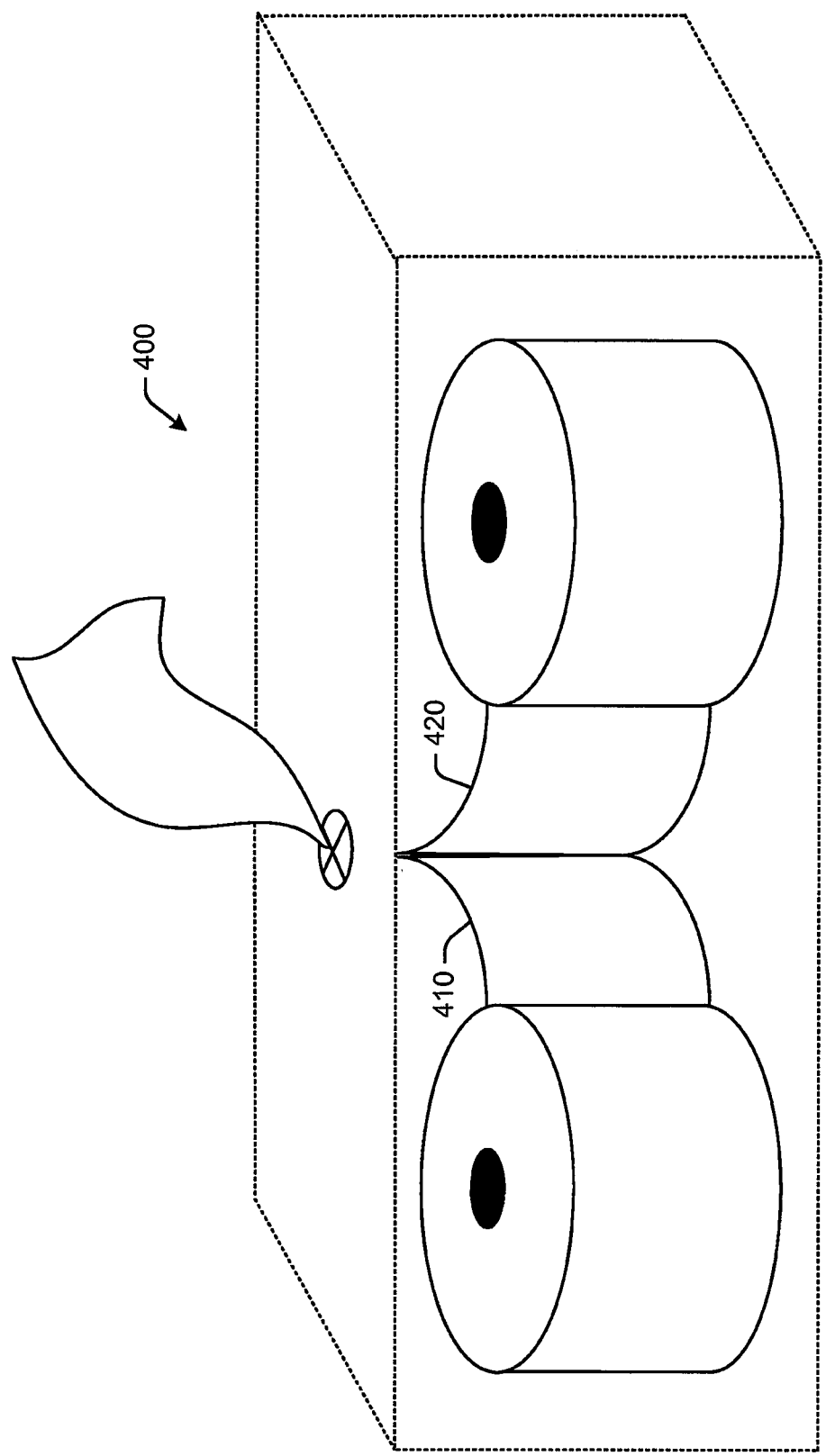
FIG. 4 is a phantom perspective view of another example dispensing system for a flavored wipe.

FIG. 4 is a phantom perspective view of another example dispensing system 400 for a flavored wipe 410. The dispensing system 400 in FIG. 4 is configured as a double sachet dispensing the material with the solution and simultaneously dispensing another material 420 with another agent (e.g., a cleaning agent), so that the two are provided on separate sheets to the user at the same time.

Figure 5:
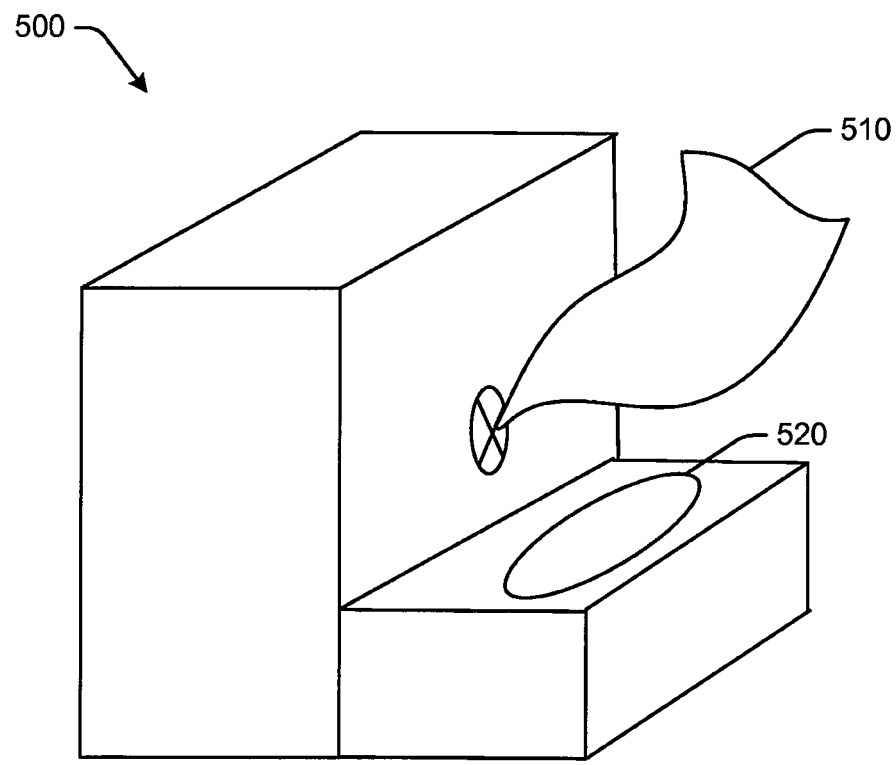
FIG. 5 is a perspective view of another example dispensing system for a flavored wipe.

FIG. 5 is a perspective view of another example dispensing system 500 for a flavored wipe 510. The dispensing system 500 in FIG. 5 is configured with another compartment 520 to contain the solution separate from the material. As such, the solution is impregnated in the material after dispensing the wipe 510 from the compartment.

Figure 6:
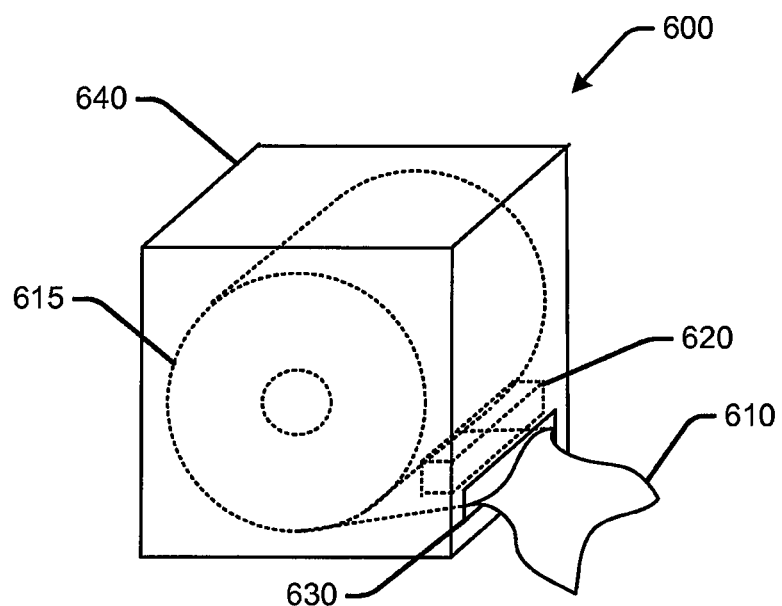
FIG. 6 is a perspective view of another example dispensing system showing the flavored wipes inside the dispensing system in phantom.
Figure 6A:
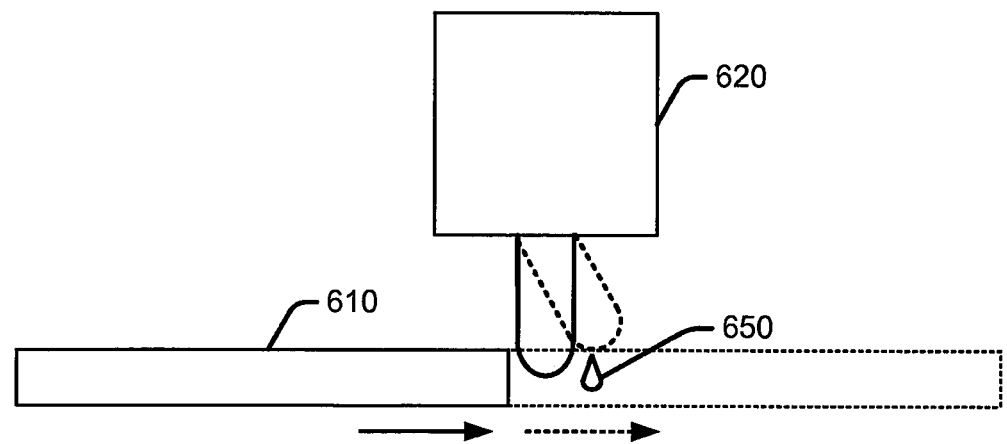
FIG. 6a is a detailed side view illustrating operation of an example applicator to apply a solution to the wipes as the wipes are dispensed from the dispensing system shown in FIG. 6.

FIG. 6 is a perspective view of another example dispensing system 600 showing the flavored wipes 610 on a roll 615 inside the dispensing system 600 in phantom. FIG. 6a is a detailed side view illustrating operation of an example applicator 620 to apply a solution (illustrated by drops 650) to the wipes 610 automatically as the wipes are dispensed from the dispensing system 600 shown in FIG. 6. In an example, the applicator 620 includes a valve (e.g., a silicon or other flexible valve) at the opening 630 of the compartment 640 which opens when moved as shown in FIG. 6 to apply solution 650 to the material as the wipe 610 travels (e.g., pulled) through the opening 630. Of course, the applicator 620 shown in FIG. 6 is illustrative and not limiting. Other manual and automatic applicators are also contemplated.

In an example, the dispensing system 600 may include a flexible plastic valve dispensing mechanism that allows only one wipe being pulled from a perforated roll within a canister. The wipe is pulled through the flexible valve. The valve creates friction and holds or "hugs" the wipe with just enough pressure to tear away one wipe at a time. The valve is soft and thus reduces or altogether prevents injury during use, such as may occur during use of metal or hard plastic wheels with teeth that grab the wipe as it is being pulled through the valve to rip the perforation. These "teethed" wheels may dispense more than one wipe, and the wipes can at times detach from the teeth so that the user has to dig it out of the canister through the valve with their finger(s). When this happens, the user is at a higher risk for hurting him or herself on the hard teeth. The user can also get their fingers stuck in the opening and when trying to pull their fingers out, the teeth can grip into the user's skin and cause pain or injury.

In an example, the valve disclosed herein may be recycled. Additionally, the valve functions more efficiently than wheels with teeth, allowing only one wipe out at a time, without the risk of the wipes falling back into the canister. Additionally, the value is more effective because it creates a more air tight seal around the wipe as it is being "hugged" to prevent the wipes within the canister from drying out. The valve opening may be made no larger than the diameter of a quarter (25 cent piece).

Figure 7:
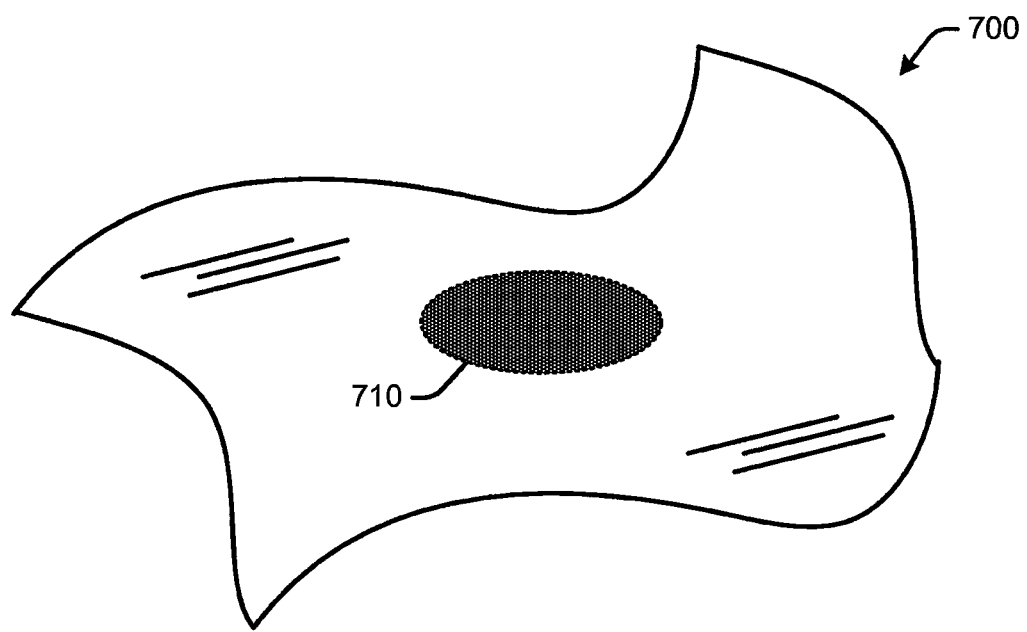
FIG. 7 is another example flavored wipe.
Figure 7A:
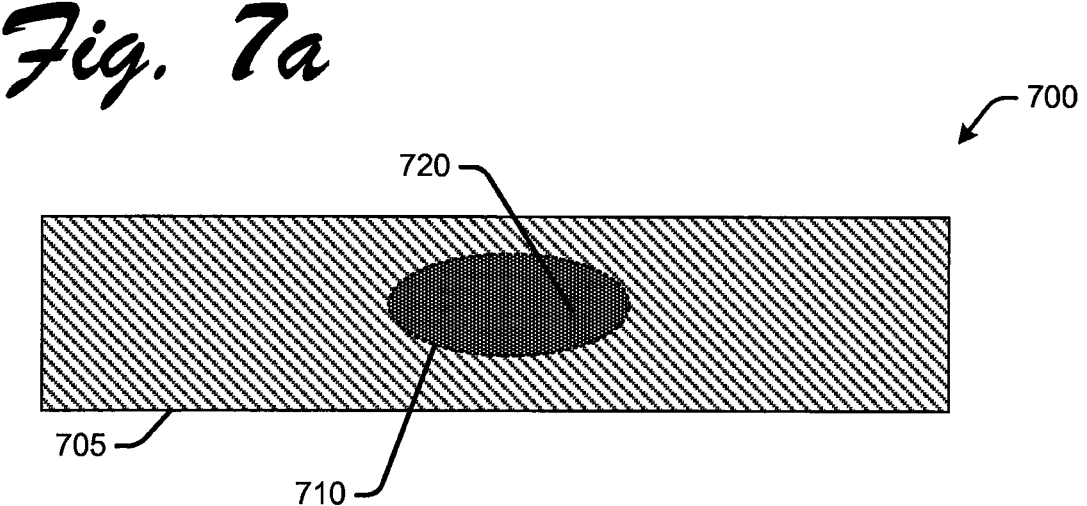
FIG. 7a is a cross-sectional view of the example flavored wipe shown in FIG. 7.

FIG. 7 is another example flavored wipe 700 showing a region 710 encapsulating the solution within the wipe 700 itself. FIG. 7a is a cross-sectional view of the example flavored wipe 700 shown in FIG. 7. In this example, the solution 720 is integral to the material 705 as a package, but not impregnated within the material. Instead, the solution is provided within region 710 in the material as a capsule (e.g., thin plastic pouch) that explodes onto the material as the wipe is dispensed (e.g., by being squeezed between rollers in the dispenser or crushed by the user's hands or other device).

As one of skill in the art will appreciate, various alternative designs and compositions can be made without departing from the scope of the present invention as encompassed by the claims. For example, in one particular embodiment, wipes (whether disposable, non woven, etc.) can be imbued with a composition of bitter oranges that contain a flavinoid that comprises neohesperidin. The hydrogenation of neohesperidin yields neohesperidin dihydrochalcolne (NHDC). NHDC is 1,500-1,800 times sweeter than sugar and exhibits synergy with other sweeteners, thereby increasing the sweetening effect and masking off-notes or bitter notes. Incorporation of at least some amounts of NHDC with respect to various embodiments of the present invention is useful for improving the overall flavor and perceived mouth feel of the wiping experience, especially with younger children and/or for adults who may be using wipes for cleaning their lips after eating especially spicy foods such as buffalo wings, etc. One particular advantage of NHDC is that it is stable over a wide range of pH's and thermal conditions and has an extended shelf life.

Still other components that may be used solely and/or in addition to the stevia components as set forth herein are the following: Monellin; miraculin; curculin; and brazzein. Monellin is a protein based sweetener that provides 1,500 times the sweetness of sugar and with only appropriately 4 calories per gram. Monellin is water soluble and possesses a lingering sweetness. Miraculin is a glycolprotein from the fruit synsepalum dulcificum, and while not a sweetener in its own right, changes the way flavors are perceived by the human tongue by binding to taste receptors. Thus, certain embodiments of the present invention employ Miraculin in combination with stevia and/or other sweeteners as described herein to enhance the desired perception of flavors. Curculin is a fruit derived protein that modifies perceived taste in a shorter time period than does Miraculin and provides sweetness around 500 times that of sucrose. Brazzein is roughly 1,000 times sweeter than sugar and has a taste profile similar to sugar with virtually no aftertaste. Brazzein exhibits great heat and acid stability and is water soluble. Thus, as otherwise explained herein, one or more of the above referenced sweeteners/proteins can be employed with stevia and/or in different combinations to provide desirable wet wipes for use in contact with human skin, especially human face and lips, either to clean undesired material from the skin of a human face or lips, and/or to soothe such human tissues after being exposed to spicy components from food, e.g., spicy buffalo wings, etc.

Monkfruit, also known as Luo Han Guo, is derived from the flesh of Siraitia Grosvenorii, and contains Mogroside V, a tri-terpene glycoside that is approximately 300 times sweeter than sugar. Monkfruit is known to resist thermal and enzymatic degradation and has no additional flavors or aftertaste, making it a valuable component when formulating various compositions as a sweetener.

Thaumatin is 2000 times as sweet as sugar and is considered GRAS in the United States. It exhibits delayed onset of intense sweetness and a lingering licorice aftertaste. Thaumatin is preferably included in various embodiments of the present invention to increase and prolong particular flavor impacts, including, but not limited to flavors of spearmint, peppermint and citrus. Thaumatin is also used in combination with various other components as described herein, including stevia, as Thaumatin improves flavor and perceived mouth feel, facilitates salt reduction by enhancing spicy notes and provides a more rounded overall flavor.

Monatin is derived from a South African plant Sclerochiton Ilicifolius and is roughly 1,400 times sweeter than sugar. Monatin provides a quick flavor onset and a clean sweetness with no aftertaste, making it well suited for use as a sweetening agent in various formulations of the present invention, including in combination with stevia.

Licorice root is available from a species of *Glycyrrhiza*, and is 50 times as sweet as sugar. Licorice root has a distinctive licorice note and is able to mask undesirable notes from other sweeteners. Thus, in various applications, licorice root is used in various combinations of the above-referenced sweeteners as described herein, including stevia for particular applications.

As otherwise described herein, a variety of different sweeteners can be combined in various and sundry combinations in order to facilitate a desired wipe having sweetness characteristics for particular applications, populations and uses. Thus, amongst the sweeteners that may be combined in various fashions are the following: Miraculin, Monelin, Advantame, Monatin, Twinsweet, stevia extract; Monkfruit, Thaumatin, Neotame, NHDC, Glycyrrhizin, APM, Cyclamate, SAC, Sucralose, and AceK.

In still other embodiments of the present invention, embodiments include the wipes as set forth herein in combination with dispensing methods and devices that make the use of such wipes far easier for various applications. For example, attachment of the present wipes of the present invention in combination with gloves, sleeves of jackets, wrist bands or arm bands, etc. can be employed. For written description and enablement purposes with respect to various types of dispensing devices for such wipes, incorporated herein by reference is U.S. Patent Publication No. 20040031120 in its entirety. In still other embodiments, the wipes of the present invention can be dispensed from a dispenser that is associated with another article, such as a bag for containing food. Again, to comply with the written description and enablement requirements, and to set forth an example of certain types of such embodiments, U.S. Patent Publication No. 20080038413 is incorporated herein in its entirety by this reference.

Also included in the present invention are various methods to employ the sweetened wipes of the present invention in new methods that enhance the eating experience of other foods. For example, the wipes of the present invention can be used to clean and/or flavor/sweeten the outer layer of a food article, such as an apple, to enhance the initial biting flavor of such a food article. To provide written description and enablement support for various methods of use of the wipes as described herein, incorporated by reference in its entirety is U.S. Pat. No. 6,821,940.

Still other embodiments of the present invention include the sweetened/flavored wipes that include embedded beads within the interior of a fibrous sheet material, with such beads comprising various active agents, including the various sweetening agents as set forth herein, including, but not limited to stevia. In alternative embodiments, such beads may be incorporated into fibrous sheets as dehydrated beads and upon hydration, such as by contacting the wipes of the present invention (in a dehydrated state) with an aqueous solution, the beads become hydrated, and ultimately rupturable, releasing their contends onto the wipe for the desired sweetness/flavoring attributes. To provide written description and enablement requirements with respect to such embodiments, incorporated by reference in its entirety is U.S. Patent Publication No. 20090286437.

Still other embodiments of the present invention also include the characteristics of such wipes as useful in reducing body odors on human skin. For example, in addition to the sweetening/flavoring components as set forth herein, such wipes may further comprise from about 0.1% to about 5% by weight of a solubilized water soluble uncomplexed cyclodextrin, alone or in combine with from about 0.5% to about 30% by weight of a linear dimethicone. In such embodiments, a wipe is provided that, unlike prior art perfume and fragrance odor devices, does not irritate a user's skin. Thus, in addition to the sweetening wipes of the present invention, other characteristics of such wipes include, in certain embodiments, compositions capable of absorbing a broad spectrum of body and environmental odors in a fashion free from irritating ingredients, such as perfumes or astringent antiperspirants, etc. To further provide written description and enablement support for such various applications, incorporated herein by reference in its entirety is PCT Publication No. PCT/US1997/018852.

Yet other embodiments of the present invention include the use of sweetened/flavored wipes, especially those including stevia, alone or in combination with the other sweeteners as set forth herein, to enhance the appearance of hair as well as skin of a human being. Thus, while prior art publications have touted the alleged appearance enhancing characteristics of orally administered stevia, the topical application of a stevia extract, especially in combination with one or more of the sweetening/flavoring components as set forth herein, provides a unique product and method for enhancing the appearance of a person's hair, without ingestion of such components orally. Incorporated herein by reference in its entirety is U.S. Patent Publication No. 20140127152, which provides background explanations with respect to the positive effects of stevia extracts (although via oral administration) to the human body and human hair.

The particular form of wipes as set forth herein include not only a traditional sized and shaped wipe dispensed from a dispenser so that individual separate wipes are pulled out of a dispenser and employed, but also various other forms of wipes dispensed in various fashions. For example, one aspect of the present invention includes the employment of a roll of wipe material that can be either torn randomly and/or along perforated lines for predetermined lengths of material for particular uses. In still other embodiments, wipes can be presented in much smaller devices, such as a swab that is sized and shaped so as to clean ears and noses, similar to pre-moistened cotton swabs.

Still other embodiments employ the use of a dispenser that includes food grade silicone that is non-hypoallergenic to a person's skin, thus preventing the contamination of wipes via the dispensing apparatus employed to retain such wipes prior to use. One particular material that may be employed for such purpose is the closed-cell foam material used, for example, in the manufacturing of the popular Crocs shoe wear. Such closed foam material, shaped in a fashion and structure so as to present a dispenser receptacle for the sweetened wipes of the present invention, is particularly preferred, as such dispenser is conformable, compressible, reusable, and preserves the desired moisture characteristics of the wipes while being retained within the dispensing receptacle. As one may appreciate with the guidance provided herein, various dispensing systems can be employed that include magnetic and/or suction based adherence devices so that dispensing apparatuses of the present wipes can be reversibly connected to various surfaces, such as tables and counters. The further advantages of such a closed foam dispensing apparatus for the wipes as set forth in the present invention include the fact that dehydrated rolls and/or stacked individual sheets of wipes can be provided within such a dispenser, and can be hydrated while inside the dispenser by mere addition of an aqueous solution at an appropriate time when a user anticipates needing such wipes. This avoids, for example, the often experienced scenario where prior art wet-wipes may have been purchased by a consumer, left in a dry environment to slowly, but surely, dehydrate, and thus become of no practical use due to the leakage of moisture from the enclosures of such wet wipe materials. In contrast to such scenarios, various embodiments of the present invention include dispensing apparatuses that can be employed to hydrate dehydrated sweetened wipes closer to the time of actual use of such wipes.

In still other embodiments, different flavored/sweetened wipes as described herein can be combined, especially in dehydrated states, and combined in a fashion such that different flavors of wipes can be rehydrated at a time such that the sweeteners and flavors of other wipes may be combined to create a rainbow of flavors as desired by a particular user. To distinguish various wipes as containing particular sweeteners and/or flavors, certain aspects of the present invention include printing and/or color coding wipes so that users understand various characteristics of such wipes, whether for instance, such wipes are of an organic, natural sweetener, artificial sweeteners, origin, or whether they include natural food dyes, are re-hydratable, combinable with other wipes to create distinct flavor profiles, etc.

With respect to various applications of use for the numerous various wipes as set forth herein, included amongst such applications are makeup wipes where individuals can employ the sweetened wipes to remove makeup, lipstick, etc. without the conventional unpleasant taste characteristics of the prior art wipes. Similarly, the wipes of the present invention can be used to remove mascara, can be employed to sooth the effects of eczema and irritated patches of a person's skin (e.g., due to the soothing characteristics of stevia and other sweeteners as set forth herein), and runners and/or athletes can employ such wipes to remove sweat, skin oils, etc. that may otherwise cause chaffing or discomfort. Other applications for newborns include employing the wipes of the present invention as a scalp cradle cap remover, with such wipes being generally moister than other wipes of the prior art, so that they are suitable for gently scrubbing away cradle cap on babies and to otherwise treat eczema conditions of a person's scalp.

Applications of the present wipe with respect to adult hair care is also contemplated, such that such wipes can be used to address dandruff conditions, whether the stevia components are used alone or in combination with other sweetening components, such as xylitol, to promote a tingling sensation on the scalp. It is believed that the use of stevia as a topical application for hair care via the wipes of the present invention is capable of strengthening hair follicles and moisturizing the scalp in a beneficial manner. It is believed that the present wipes used in such a fashion (rather than an oral administration of stevia) can reduce hair loss and strengthen the condition of the dermus and hair in a beneficial manner, especially if such wipes are used on a daily or bi-daily basis.

Still other uses of the present wipes include particular wipes for musical instruments whereby human mouths are contacted with such instruments. For example, particular "music wipes" may be specially formulated for use with bamboo inserts into wind instruments, as well as cleaning the external mouthpieces of trumpets, tubas, oboes, flutes and various other mouth related musical instruments. The desirable taste imparted by the wipes on such musical instruments is not only pleasant, but also wipes away the unpleasant bacterial contamination and odors associated therewith, resulting from resident human saliva left to dry on such musical instrument surfaces.

Still other uses of the present sweetened/flavored wipes include use in rolling of cigarettes, cigars, cannabis related devices, etc. where especially stevia wipes may be provided in a dehydrated state such that the sweetness appreciated by a user would be experienced upon moisturization of such wipes via mouth contact. In a similar manner, the wipes of the present invention find application in cleaning and thereby sweetening the surfaces of various smoking and/or inhalation devices, such as pipes, apparatuses, bongs, and various other inhalement devices. In the medical device context, the sweetened wipes find application in hospital settings as well as in in-home health care and hospice care, whereby sweetened wipes are useful in cleaning tubes or other mouth contacting appliances employed in such settings.

In neonatal ICU units, instead of employing sugar drops, the sweetened wipes of the present invention can be employed to wipe on a newborn's lips so they are able to calm down and sit long enough for various medical procedures, such as an EKG. At the opposite end of the human life, the sweetened wipes of the present invention find various applications in nursing homes, where aged individuals are desirous of wipes to address cleaning of their lips and face due to often difficult eating regiments due to strokes, Parkinson's, Alzheimer's, etc.

Various applications of the present application include the use of sweetened wipes for outdoorsman, such as hunters, fisherman and camping enthusiasts where sweetened wipes find application in the cleaning of human body parts due to the variety of dirt, blood, fish slime, etc. that would otherwise be addressed if a source of running water were available, but without such source, the sweetened wipes of the present invention provide a desirable alternative to the traditional alcohol based and/or soap based wipes of the prior art. As set forth in the specification, use of a spray to enhance the stevia and/or other sweetener compositions onto a wipe material is within the scope of the present invention and finds particular application for skin plumping, or otherwise providing a salve for a person's skin, as stevia has inherent skin moisture enriching attributes and if used in combination with xylitol, has a tingling effect on a human's skin, and thus acts as a "freshen up" aspect, rather than the traditional alcohol/soapy residues left by more traditional wipes.

In yet other applications in the veterinary field, animal bit wipes may be employed for horses. Sweetened wipes also find application with domestic animals such as dogs and cats, such that a more pleasant experience is provided to such pets, including wiping of bottle nipples to provide the desired sweetness of such nipples in administering milk formulations to small animals during weaning and feeding thereof.

It is to be noted that in particular embodiments, stevia sweetener employed on a wipe is not blended with erythritol, as such a combination is believed to be distasteful and is to be avoided. Other natural sweeteners, however, in combination with stevia, are particularly desired, such that one or more of the following combined with stevia on the various wipes/swabs as set forth in the present invention are particularly desired: dehydrated fruit extracts, raw honey extracts, maple sugar, coconut palm sugar, corn based sweeteners, cane or beet sugar, agave (whether in oil, extract, powder, nectar or sugar form), honey based sweeteners, rice based sweeteners, anti-oxidant compounds, such as those found in Monkfruit, mogroside based sweeteners, aspartame, natural fruit based sweeteners, molasses based sweeteners, sucralose, acesulfame-K, isomaltulose, barley malt, coconut based sweeteners, grapefruit rind extract, citrus juices, fruit juices, root bark, vanillian, glucose, fructose, lactose, maltose, sucrose, dextrose, malt extracts, humectants sweeteners, and other sweeteners having a significant hygroscopicity.

Yet another embodiment of the present invention relates to a thick bracelet/cuff style carrying case that can distribute wipes of the present invention, such carrying case preferably made form EVA material. In a preferred embodiment, such a bracelet/cuff would be fashionably designed such that athletes, bikers, etc. would wear such a bracelet at local gyms while working out, playing tennis, golf, etc. and would therefore have ready access to a compartment having the wipes of the present invention for easy use thereof. In a preferred embodiment, the bracelet is maintained in a slim design and only carries at any given time 3-4 wipes, thus a person wearing such a bracelet would have ready access to a few wipes in a handy manner without having to lug a purse or other backpack or other container that might include a larger dispensing unit.

Such a bracelet/wrist surrounding device (although it could be designed so as to be fastened around ankles, arms and other body parts) is preferably constructed of ethylene vinyl acetate (EVA) which is a polymer that has elastomeric characteristics and is soft and flexible, stress/crack resistant and waterproof. Particular dispensers of the wipes as described herein, is particularly advantageous in such an EVA bracelet dispenser as busy mothers would then always have at least a few of the sweetened wipes for use with their children even though the mother may be separated from her purse, automobile, etc. where a larger dispensing unit for such wipes may be located. To comply with written description and enablement requirements, the inventors incorporate by reference in its entirety U.S. Pat. No. 7,735,682 for representative types of a wipe dispenser for use with the novel wipes as set forth herein.

Still other embodiments of the present invention are directed to methods and products, in particular wipes for child as well as adult purposes, that are designed so as to reduce the amount of a sweetener included in such wipes by, for example, enhancing, modulating or potentiating the sweet taste of a substance provided on a wipe, such as described herein, but especially a food contacting wipe, and other consumer or pharmaceutical related products. Thus, various aspects of the present invention are directed to products produced using a method of modulating, particularly enhancing or potentiating the activation of a sweet taste receptor.

In various embodiments, compounds are included and are contacted with a wipe for modulating sweet taste (e.g., enhancing sweet taste), including flavonoid compounds, such as a flavanone, flavan, flavanol (such as flavan-4-ol), anthocyanin or benzodioxan (such as a 1,3-benzodioxane). In some embodiments, the flavonoid compound has a molecular weight less than about 1000, 500, or 300 daltons, and in others, includes comestibly or biologically acceptable salts or derivatives thereof, enantiomers or diastereomers thereof, or combinations thereof. In some embodiments, the flavonoid compound has a molecular weight less than about 1000, 500, or 300 daltons. As one of skill will appreciate, taste modulators may be combined with any suitable sweetener, such as a natural caloric sweetener, a natural high-potency sweetener, a synthetic sweetener including a synthetic high-potency sweetener, stevia, sugar alcohols, rare sugars, sweetener enhancers or combinations thereof, to provide a composition having enhanced sweetness. Other aspects of the present invention are directed to providing a method of enhancing the sweetness of a sweetener comprising combining (i) at least one sweetener, such as a natural caloric sweetener, a natural high-potency sweetener, a synthetic sweetener including a synthetic high-potency sweetener, stevia, sugar alcohols, rare sugars, sweetener enhancers or combinations thereof, and (ii) a flavonoid sweet taste modulator and (iii) at least one sweet taste improving composition. The following are incorporated herein in their entireties by this reference to provide additional written description and enablement support for various embodiments of the present invention: Luo et al, U.S. Pat. Publication No. 20150050410; 20150011493 to Laboureau et al.

In still other embodiments, the present invention finds application in the field of cosmetic active agents and more particularly active agents devoted to acting with regard to aging of the skin, and especially as administered through a wipe as described herein. The human skin consists of several layers, including the epidermis, the dermis and the hypodermis. The epidermis is a keratinized stratified pavement epithelium. It is composed mainly of keratinocytes but also of other cells and rests on a basal membrane which separates it from the dermis. The dermis is a connective tissue. Its architecture results from the arrangement and the interactions between the constituents of the extracellular matrix and the fibroblasts, which carry out the synthesis thereof and the degradation thereof. It makes up the main bulk of skin. The dermis is subdivided into two layers, the papillary layer and the reticular layer. The dermis is composed of collagen fibers and elastin fibers, and also of glycosaminoglycans and proteoglycans. These different structures form a complex network which plays a key role in the biomechanical properties of the skin. Finally, the hypodermis, the deepest layer and generally the thickest layer of the skin, invaginates into the dermis and is attached to the overlying dermis via collagen and elastin fibers and it is largely composed of a type of cells which are specialized in the accumulation and storage of fats, the adipocytes. In the region where the tegumentary covering is not keratinized, the epidermis is referred to as mucus membrane. This epithelium also comprises fibroblasts within a dermal matrix. Skin tissue also comprises appendages, such as sweat glands, pilosebaceous follicles, body hair, head hair and nails.

When skin ages, the dermis is subjected to numerous modifications and types of damage. In particular, numerous detrimental changes in the skin, resulting from a dysfunctioning of its homeostasis and in particular from a dysfunctioning of the metabolism of the fibroblasts, occur. Detrimental changes occur as one ages, especially to fibroblasts and the keratinocytes, causing issues with blood irrigation and innervation systems, and a slowing down of various types of metabolism, such as those involved in the equilibrium of the barrier function. This process results in the appearance of wrinkles and fine lines and a decrease in firmness and elasticity, as well as a decrease in the thickness of the skin and a consequent reduction in the radiance of the complexion of the skin. One's skin may also be detrimentally affected by menopause, which may result in skin exhibiting a rough aspect to the touch and reduced suppleness.

Thus, one aspect of the present invention is to provide a product, in particular a wipe, that is capable of effectively acting on a person's skin cells in a manner that limits the detrimental changes otherwise observed due to aging. In various embodiments, stevia, steviol, a steviol glycoside derivative or one of their isomers, alone or in combinations with other substances and compounds as set forth herein, are employed in various ways, and in particular in combination with wipes as described herein, to prevent and/or treat disorders related to skin aging and to enhance the natural beauty of a person's skin. It will be understood by one of skill in the art that referenced combinations include, for example, all steviol/steviosides/compounds in stevia, etc., whether they are extracted naturally, fermented to enhance the steviosides or grown in a lab or unnatural environment. While not bound by theory, it is believed that stevia-like compositions, such as steviol, a steviol glycoside derivative or one of their isomers effectively brings about contraction of the fibroblasts, thus reducing the occurrence of deep wrinkles and the loss in firmness of the skin, apparently by stimulating the regeneration processes of the body to combat the appearance of signs of aging of the skin.

The particular cosmetic uses of the wipes as described herein are thus believed to be considerable, especially with respect to the sensitive tissues of a person's lips, or other mucas membranes or semimucus membranes. It is further believed that use of the wipes as described herein is useful in addressing skin damage resulting from ultra violet radiation, especially derived from the sun, for example, wrinkles and fine lines, withered skin, flabby skin, thinned skin, lack of elasticity and/or tonicity of the skin or lack of density and/or firmness of the skin. In addition, via topical application of compounds present in the various wipes as described herein, other health benefits are believed to be possible, e.g. rebaudioside A is a molecule of interest in regulating glycemia or the metabolism of the cells of the pancreas and treating diabetes (Abudula et al., Metabolism, 2004, 53, 1378; WO 02/060419), and in improving cognitive functions (WO 2009/071277) or in treating cardiovascular diseases (WO 2008/134828), treating greasy skin or acne by regulating the metabolism of the sebocytes (U.S. Pat. No. 5,110,801), promoting the penetration of vitamin C into cells (WO 07/094,312) and in combating inflammatory phenomena (allergy, dermatitis) (JP-08325156-A); with all of these referenced patent publications hereby incorporated in their entireties by this reference.

As one will appreciate in view of the guidance and disclosure set forth herein, various embodiments of the present invention include the use of stevia and all of its potential forms, including all species of Rebaudiosides, and variants thereof. In particular, in various embodiments, powdered sweetener compounds are included, especially in combination with various stevia formulations, and especially compounds that include the dissolution of sweeteners in order to promote stability of the final product, with such dissolution of sweeteners being either in a water based or organic-type solvent. As one will appreciate, numerous well known extraction methods can be employed to obtain desired stevia formulations and compounds, including, but not limited to, lab produced versions, organically grown fermented processes, etc. In certain embodiments, stevia is combined with a naturally derived, high performance surfactant, such as Sugarnate™, which is especially preferred due to its avoidance of irritation to a person's eyes and skin, and with a very low toxicity as compared to other surfactants.

In various embodiments of the present invention, stevia is included with an erythrithol-based sweetener composition and is then employed in the various different ways as set forth in the present specification, including in combination with wipes, cosmetic applications, etc., and to provide written description and enablement parameters, U.S. Patent Publication No. 2009/004355 to Catani is incorporated herein in its entirety by this reference. Similarly, fermented stevia solutions can be obtained in various processes, including that disclosed in Patent Publication No. WO2005/089782, to Kouzou, which is also incorporated herein in its entirety by this reference. Also incorporated herein by this reference is U.S. Patent Publication No. 2013/0071887 to Wehrli, for other methods to produce steviol using commercially available enzyme mixtures. Also incorporated herein by this reference in its entirety is U.S. Patent Publication No. 2014/0227421 to Markosyan, especially with respect to the various derivatives of stevia extract, including but not limited to rebaudioside A-Z, and in particular, Reb A, B, C, D, E, F, M, N and O.

It is also noted that many of the structures, materials, and acts recited herein can be recited as means for performing a function or step for performing a function. Therefore, it should be understood that such language is entitled to cover all such structures, materials, or acts disclosed within this specification and their equivalents, including any matter incorporated by reference.

It is thought that the apparatuses and methods of embodiments described herein will be understood from this specification. While the above description is a complete description of specific embodiments, the above description should not be taken as limiting the scope of the patent as defined by the claims.

It will be understood that while embodiments have been described in conjunction with specific examples, the foregoing description and examples are intended to illustrate, but not limit the scope of the invention. Other aspects, advantages, and modifications will be apparent to those of ordinary skill in the art to which the claims pertain. The elements and use of the above-described embodiments can be rearranged and combined in manners other than specifically described above, with any and all permutations within the scope of the disclosure.

What is claimed is:

1. A flavored wipe, comprising:
   a wipe material made from nonwoven cloth material;
   said wipe material contacted with a solution comprising water and a flavoring component, said flavoring component including at least a sweetener comprising a stevia solution prepared by combining a stevia extract selected from the group consisting of Rebaudioside-A, Rebaudioside-C, Rebaudioside-D, and Stevioside, said stevia extract contributing from at least 0.1% by weight of the solution.

2. The flavored wipe as set forth in claim 1, further comprising at least one substance selected from the group consisting of honeysuckle extract; vitamin E, chamomile, aloe vera, polysorbate 80, annatto Extract, orange oil, sugarnat, polysorbate 80, sodium benzoate and green tea extract.

3. The flavored wipe as set forth in claim 1, wherein said wipe is contained in a dispenser having an opening, said dispenser adapted to hold a plurality of said wipes and having a means for releasably sealing said opening to prevent said wipes from drying out.

4. The flavored wipe as set forth in claim 3, wherein said dispenser is adapted to be worn about a person's wrist.

5. The flavored wipe of claim 1, wherein the flavoring component is Rebaudioside-A.

6. The flavored wipe of claim 1, wherein the flavoring component further comprises a cleaning additive.

7. The flavored wipe of claim 1, wherein the flavoring component further comprises a skin moisturizer.

8. The flavored wipe of claim 1, wherein the material is a dry wipe and the flavoring component is added to the material by spraying.

9. The flavored wipe of claim 1, wherein the material configured for use as a wipe is resistant to microbial growth.

10. The flavored wipe of claim 1, wherein the material configured for use as a wipe has anti-pathogen properties.

11. The flavored wipe of claim 1, wherein the wipe does not irritate skin of a user and is biodegradable.

12. The flavored wipe of claim 1, wherein the wipe includes steviol and the use of the wipe reduces the appearance of wrinkles.

13. The flavored wipe of claim 1, wherein the wipe is configured with stevia to moisturize and soothe and clean skin.

14. The flavored wipe of claim 1, further comprising at least one of the group consisting of potassium sorbate, sodium benzoate, and decyl glycoside.

15. The flavored wipe of claim 1, wherein said solution is 90% water by weight.

16. The flavored wipe of claim 1, wherein said solution further comprises at least one of Luo han guo, Mogrosides, Monk Fruit, Monatin, Cyclamate, and Brazzein.

17. The flavored wipe of claim 1, wherein the flavoring component further comprises at least one artificial sweetener.

18. A flavored wipe, comprising:
    a wipe material made from nonwoven cloth material;
    said wipe material contacted with a solution comprising water and a flavoring component, said flavoring component including at least a sweetener comprising a stevia solution prepared by combining a stevia extract selected from the group consisting of Rebaudioside-A, Rebaudioside-C, Rebaudioside-D, and Stevioside.

19. The flavored wipe of claim 18, wherein said solution further comprises at least one of Luo han guo, Mogrosides, Monk Fruit, Monatin, Cyclamate, and Brazzein, honeysuckle extract; vitamin E, chamomile, aloe vera, polysorbate 80, annatto Extract, orange oil, sugarnate, polysorbate 80, sodium benzoate and green tea extract.

20. The flavored wipe of claim 18, wherein said solution further comprises at least one of a cleaning agent, a moisturizing agent, a coloring agent and a scenting agent.

* * * * *